US011786676B2

(12) United States Patent
Patton et al.

(10) Patent No.: US 11,786,676 B2
(45) Date of Patent: Oct. 17, 2023

(54) METHODS AND SYSTEMS FOR SUPPLYING AEROSOLIZATION DEVICES WITH LIQUID MEDICAMENTS

(71) Applicant: Aerami Therapeutics, Inc., Durham, NC (US)

(72) Inventors: Ryan S. Patton, San Francisco, CA (US); John S. Patton, San Francisco, CA (US); Mei-chang Kuo, Palo Alto, CA (US); Yehuda Ivri, Newport Beach, CA (US)

(73) Assignee: Aerami Therapeutics, Inc., Durham, NC (US)

( * ) Notice: Subject to any disclaimer, the term of this patent is extended or adjusted under 35 U.S.C. 154(b) by 236 days.

(21) Appl. No.: 16/133,484

(22) Filed: Sep. 17, 2018

(65) Prior Publication Data

US 2019/0015611 A1    Jan. 17, 2019

Related U.S. Application Data

(63) Continuation-in-part of application No. 15/165,662, filed on May 26, 2016, now Pat. No. 10,525,214, (Continued)

(51) Int. Cl.
*A61M 15/00* (2006.01)
*A61M 11/00* (2006.01)

(52) U.S. Cl.
CPC ...... *A61M 15/0085* (2013.01); *A61M 11/005* (2013.01); *A61M 15/0065* (2013.01); *A61M 2209/045* (2013.01)

(58) Field of Classification Search
CPC .......... A61M 15/0085; A61M 15/0028; A61M 21/00; A61M 2205/502;
(Continued)

(56) References Cited

U.S. PATENT DOCUMENTS 1,947,310 A    2/1934  Sample et al.
2,463,922 A *  3/1949  Turner .................... B67D 3/02
                                            141/288
(Continued)

FOREIGN PATENT DOCUMENTS

BR    112012017177 B1    10/2020
BR    112014025878 B1    4/2022
(Continued)

OTHER PUBLICATIONS

"ON" Oxforadictinaries.com., Oxford Dictionaries, 2016, Web. Jun. 21, 2016, 1 page.
(Continued)

*Primary Examiner* — Valerie L Woodward
(74) *Attorney, Agent, or Firm* — KILPATRICK TOWNSEND & STOCKTON LLP

(57) ABSTRACT

A method is described for supplying a metered amount of a liquid medicament to an aerosolizing device. The method utilizes a dispenser comprising an elongate dispenser body having a proximal end and a tip at a distal end through which a liquid medicament is dispensed. The dispenser further comprises a dispensing mechanism that operates to dispense a metered quantity of the liquid medicament from the tip each time the dispenser body is compressed. The dispenser is grasped with one hand such that the fingers wrap around the dispenser body, with the thumb closest to the proximal end and the last finger closest to the tip. The tip is inserted into an opening of an inhaler and the elongate body is forced toward the tip to cause the dispenser body to compress, thereby operating the dispensing mechanism and causing a metered quantity of the liquid medicament to eject into the inhaler.

20 Claims, 5 Drawing Sheets

Related U.S. Application Data which is a continuation of application No. 14/606,623, filed on Jan. 27, 2015, now Pat. No. 9,545,488, which is a continuation of application No. 14/039,254, filed on Sep. 27, 2013, now Pat. No. 9,004,061, said application No. 16/133,484 is a continuation of application No. 13/830,511, filed on Mar. 14, 2013, now abandoned, said application No. 14/039,254 is a continuation of application No. 13/004,662, filed on Jan. 11, 2011, now Pat. No. 8,950,394.

(60) Provisional application No. 61/624,531, filed on Apr. 16, 2012, provisional application No. 61/335,769, filed on Jan. 12, 2010.

(58) Field of Classification Search
CPC ...... A61M 2021/0027; A61M 2230/63; A61M 2021/0016; A61M 15/001; A61M 15/0065; A61M 11/005; B05B 7/2489
See application file for complete search history.

(56) References Cited

U.S. PATENT DOCUMENTS

| | | |
|---|---|---|
| 3,789,843 A | 2/1974 | Armstrong et al. |
| 3,874,380 A | 4/1975 | Baum |
| 4,564,129 A | 1/1986 | Urban et al. |
| 4,694,977 A | 9/1987 | Graf et al. |
| 5,060,642 A | 10/1991 | Gilman |
| 5,164,740 A | 11/1992 | Ivri |
| 5,261,601 A | 11/1993 | Ross et al. |
| 5,333,106 A | 7/1994 | Lanpher et al. |
| 5,347,998 A | 9/1994 | Hodson et al. |
| 5,363,842 A | 11/1994 | Mishelevich et al. |
| 5,364,838 A | 11/1994 | Rubsamen |
| 5,385,180 A | 1/1995 | Wittman et al. |
| 5,479,920 A | 1/1996 | Piper et al. |
| 5,487,378 A | 1/1996 | Robertson et al. |
| 5,515,842 A | 5/1996 | Ramseyer et al. |
| 5,586,550 A | 12/1996 | Ivri et al. |
| 5,672,581 A | 9/1997 | Rubsamen et al. |
| 5,694,919 A | 12/1997 | Rubsamen et al. |
| 5,743,250 A | 4/1998 | Gonda et al. |
| 5,758,637 A | 6/1998 | Ivri et al. |
| 5,809,997 A | 9/1998 | Wolf |
| 5,884,620 A | 3/1999 | Gonda et al. |
| 5,915,378 A | 6/1999 | Lloyd et al. |
| 5,938,117 A | 8/1999 | Ivri |
| 5,941,240 A | 8/1999 | Gonda et al. |
| 6,014,970 A | 1/2000 | Ivri et al. |
| 6,062,212 A | 5/2000 | Davison |
| 6,085,740 A | 7/2000 | Ivri et al. |
| 6,085,753 A | 7/2000 | Gonda et al. |
| 6,098,615 A | 8/2000 | Lloyd et al. |
| 6,131,567 A | 10/2000 | Gonda et al. |
| 6,164,498 A * | 12/2000 | Faughey ............. B05B 11/3008 222/153.13 |
| 6,205,999 B1 | 3/2001 | Ivri et al. |
| 6,257,454 B1 | 7/2001 | Ritsche |
| 6,312,665 B1 | 11/2001 | Modi |
| 6,408,854 B1 | 6/2002 | Gonda et al. |
| 6,427,682 B1 | 8/2002 | Klimowicz et al. |
| 6,467,476 B1 | 10/2002 | Ivri et al. |
| 6,540,153 B1 | 4/2003 | Ivri |
| 6,540,154 B1 | 4/2003 | Ivri et al. |
| 6,629,646 B1 | 10/2003 | Ivri |
| 6,640,804 B2 | 11/2003 | Ivri et al. |
| 6,647,987 B2 | 11/2003 | Gonda et al. |
| 6,688,304 B2 | 2/2004 | Gonda et al. |
| 6,712,762 B1 | 3/2004 | Lichter et al. |
| 6,729,327 B2 | 5/2004 | McFarland, Jr. |
| 6,748,946 B1 | 6/2004 | Rand et al. |
| 6,755,189 B2 | 6/2004 | Ivri et al. |
| 6,790,178 B1 | 9/2004 | Mault et al. |
| 6,814,071 B2 | 11/2004 | Klimowicz et al. |
| 6,921,020 B2 | 7/2005 | Ivri |
| 6,926,208 B2 | 8/2005 | Ivri |
| 6,958,691 B1 | 10/2005 | Anderson et al. |
| 6,978,941 B2 | 12/2005 | Litherland et al. |
| 7,028,686 B2 | 4/2006 | Gonda et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,083,112 B2 | 8/2006 | Ivri |
| 7,100,600 B2 | 9/2006 | Loeffler et al. |
| 7,108,197 B2 | 9/2006 | Ivri |
| 7,117,867 B2 | 10/2006 | Cox et al. |
| 7,174,888 B2 | 2/2007 | Ivri et al. |
| 7,195,011 B2 | 3/2007 | Loeffler et al. |
| 7,219,664 B2 | 5/2007 | Ruckdeschel et al. |
| 7,448,375 B2 | 11/2008 | Gonda et al. |
| 7,451,760 B2 | 11/2008 | Denyer et al. |
| 7,600,511 B2 | 10/2009 | Power et al. |
| 7,600,512 B2 | 10/2009 | Lee et al. |
| 7,628,339 B2 | 12/2009 | Ivri et al. |
| 7,683,029 B2 | 3/2010 | Hindle et al. |
| 7,819,115 B2 | 10/2010 | Sexton et al. |
| 7,886,783 B2 | 2/2011 | Rindy et al. |
| 8,082,918 B2 | 12/2011 | Jansen et al. |
| 8,326,964 B1 | 12/2012 | Chourey |
| 8,736,227 B2 | 5/2014 | Chadbourne et al. |
| 8,950,394 B2 | 2/2015 | Patton et al. |
| 9,004,061 B2 | 4/2015 | Patton et al. |
| 9,180,261 B2 | 11/2015 | Patton et al. |
| 9,545,488 B2 | 1/2017 | Patton et al. |
| 10,525,214 B2 | 1/2020 | Patton et al. |
| 11,400,241 B2 | 8/2022 | Patton et al. |
| 2001/0037805 A1 | 11/2001 | Gonda et al. |
| 2001/0039948 A1 | 11/2001 | Sexton et al. |
| 2002/0129813 A1 | 9/2002 | Litherland |
| 2003/0019493 A1 | 1/2003 | Narayan et al. |
| 2003/0041859 A1 | 3/2003 | Abrams et al. |
| 2003/0072740 A1 | 4/2003 | Milstein et al. |
| 2003/0101991 A1 | 6/2003 | Trueba |
| 2003/0150445 A1* | 8/2003 | Power ............... A61M 16/049 128/200.14 |
| 2003/0150446 A1 | 8/2003 | Patel et al. |
| 2004/0100509 A1 | 5/2004 | Sommerer |
| 2004/0134494 A1 | 7/2004 | Papania et al. |
| 2004/0154617 A1 | 8/2004 | Enk |
| 2004/0223917 A1 | 11/2004 | Hindle et al. |
| 2004/0256488 A1 | 12/2004 | Loeffler et al. |
| 2005/0011514 A1 | 1/2005 | Power et al. |
| 2005/0030953 A1 | 2/2005 | Vasudevan et al. |
| 2005/0133024 A1 | 6/2005 | Coifman |
| 2005/0166913 A1 | 8/2005 | Sexton et al. |
| 2005/0172958 A1 | 8/2005 | Singer et al. |
| 2005/0240084 A1 | 10/2005 | Morice et al. |
| 2006/0239930 A1 | 10/2006 | Lamche et al. |
| 2006/0261084 A1 | 11/2006 | Grey et al. |
| 2007/0074722 A1 | 4/2007 | Giroux et al. |
| 2007/0113841 A1 | 5/2007 | Fuchs |
| 2007/0163572 A1* | 7/2007 | Addington ............. A61M 11/02 128/200.14 |
| 2007/0209659 A1 | 9/2007 | Ivri et al. |
| 2008/0017188 A1 | 1/2008 | Pardonge et al. |
| 2008/0020794 A1 | 1/2008 | Garon et al. |
| 2008/0029083 A1 | 2/2008 | Masada et al. |
| 2008/0060641 A1 | 3/2008 | Smith et al. |
| 2008/0148193 A1 | 6/2008 | Moetteli |
| 2008/0184993 A1 | 8/2008 | Patel |
| 2008/0220747 A1 | 9/2008 | Ashkenazi et al. |
| 2008/0233053 A1 | 9/2008 | Gross et al. |
| 2008/0306794 A1 | 12/2008 | Cohen et al. |
| 2009/0025718 A1 | 1/2009 | Denyer |
| 2009/0095292 A1 | 4/2009 | Hamano et al. |
| 2009/0099065 A1 | 4/2009 | Madsen et al. |
| 2009/0140010 A1 | 6/2009 | Pruvot |
| 2009/0151718 A1 | 6/2009 | Hunter et al. |
| 2009/0156952 A1 | 6/2009 | Hunter et al. |
| 2009/0157037 A1 | 6/2009 | Iyer et al. |
| 2009/0194104 A1 | 8/2009 | Van Sickle |
| 2009/0241948 A1 | 10/2009 | Clancy |
| 2009/0301472 A1 | 12/2009 | Kim et al. |

(56) References Cited

U.S. PATENT DOCUMENTS

| | | |
|---|---|---|
| 2010/0075001 A1 | 3/2010 | Succar et al. |
| 2010/0094099 A1 | 4/2010 | Levy et al. |
| 2010/0153544 A1 | 6/2010 | Krassner et al. |
| 2010/0154793 A1 | 6/2010 | Kobayashi et al. |
| 2010/0180890 A1 | 7/2010 | Nobutani |
| 2010/0236545 A1 | 9/2010 | Kern |
| 2010/0250280 A1 | 9/2010 | Sutherland |
| 2010/0250697 A1 | 9/2010 | Hansen et al. |
| 2010/0319686 A1 | 12/2010 | Schennum |
| 2010/0326436 A1 | 12/2010 | Kaneko |
| 2011/0022350 A1 | 1/2011 | Chatterjee |
| 2011/0114089 A1 | 5/2011 | Andersen et al. |
| 2011/0125594 A1 | 5/2011 | Brown et al. |
| 2011/0168172 A1 | 7/2011 | Patton et al. |
| 2011/0225008 A1 | 9/2011 | Elkouh et al. |
| 2011/0246440 A1 | 10/2011 | Kocks et al. |
| 2011/0253139 A1 | 10/2011 | Guthrie et al. |
| 2012/0032901 A1 | 2/2012 | Kwon |
| 2012/0037154 A1 | 2/2012 | Gallem et al. |
| 2012/0069803 A1 | 3/2012 | Iwamura et al. |
| 2012/0116241 A1 | 5/2012 | Shieh |
| 2012/0144303 A1 | 6/2012 | Cricks et al. |
| 2012/0155987 A1 | 6/2012 | Watanabe |
| 2012/0285236 A1 | 11/2012 | Haartsen et al. |
| 2013/0155987 A1 | 6/2013 | Lan et al. |
| 2013/0318471 A1 | 11/2013 | Freyhult |
| 2014/0010187 A1 | 1/2014 | Huang et al. |
| 2014/0362831 A1 | 12/2014 | Young |
| 2015/0092590 A1 | 4/2015 | Zhu et al. |
| 2015/0196721 A1 | 7/2015 | Patton et al. |
| 2019/0015611 A1 | 1/2019 | Patton et al. |

FOREIGN PATENT DOCUMENTS

| | | |
|---|---|---|
| CN | 1062091 | 6/1992 |
| CN | 2406684 Y | 11/2000 |
| CN | 1303309 | 7/2001 |
| CN | 2461580 | 11/2001 |
| CN | 101080249 | 11/2007 |
| CN | 101300041 | 11/2008 |
| CN | 101316660 | 12/2008 |
| CN | 101495168 | 7/2009 |
| CN | 102740915 B | 1/2016 |
| EP | 111875 | 6/1984 |
| EP | 311863 | 4/1989 |
| EP | 2838593 A1 | 2/2015 |
| EP | 2838592 B1 | 5/2018 |
| FR | 2 835 435 A1 | 8/2003 |
| MX | 340395 B | 7/2016 |
| RU | 2188041 | 8/2002 |
| RU | 2336906 | 10/2008 |
| RU | 2460677 | 9/2012 |
| WO | 98/22290 A1 | 5/1998 |
| WO | 03/030829 A2 | 4/2003 |
| WO | 2004/028608 | 4/2004 |
| WO | 2005065756 | 7/2005 |
| WO | 2006/062449 | 6/2006 |
| WO | 2006006963 | 6/2006 |
| WO | 2007/047948 A2 | 4/2007 |
| WO | 2008121610 | 10/2008 |
| WO | 2009/111612 A1 | 9/2009 |
| WO | 2010002421 | 1/2010 |
| WO | 2010/066714 A1 | 6/2010 |
| WO | 2010141803 | 12/2010 |
| WO | 2011088070 A1 | 7/2011 |
| WO | 2011130183 | 10/2011 |

OTHER PUBLICATIONS

Australian Application No. 2011205443, First Examination Report dated Mar. 13, 2015, 3 pages.
Chinese Application No. 201180005839.9, Notice of Decision to Grant dated Sep. 18, 2015, 4 pages (3 pages for the original document and 1 page for the English translation).
Chinese Application No. 201380031812.6, Office Action dated Apr. 19, 2016, 6 pages.
Indian Application No. 1921/MUMNP/2012, First Examination Report dated May 10, 2019, 7 pages.
International Application No. PCT/US2011/020925, International Preliminary Report on Patentability dated Jul. 26, 2012, 6 pages.
International Application No. PCT/US2011/020925, International Search Report and Written Opinion dated Mar. 14, 2011, 7 pages.
International Application No. PCT/US2013/034359, International Preliminary Report on Patentability dated Oct. 30, 2014, 7 pages.
Mexican Application No. MX/A/2012/008010, Office Action dated Feb. 12, 2015, 2 pages.
Mexican Application No. MX/A/2012/008010, Office Action dated Jul. 15, 2014, 5 pages.
Russian Application No. 2012134422, Notice of Decision to Grant dated Feb. 17, 2015, 13 pages (8 pages for the original document and 5 pages for the English translation).
Russian Application No. 2014145835, Office Action dated Feb. 6, 2017, 7 pages.
Russian Application No. 2014145836, Notice of Decision to Grant dated Jul. 27, 2017, 8 pages.
U.S. Appl. No. 13/004,662, Advisory Action dated Sep. 6, 2013, 3 pages.
U.S. Appl. No. 13/840,588, Final Office Action dated Sep. 11, 2015, 30 pages.
U.S. Appl. No. 13/840,588, Final Office Action dated Jun. 30, 2016, 32 pages.
U.S. Appl. No. 3/840,588, Non-Final Office Action dated Feb. 24, 2016, 15 pages.
U.S. Appl. No. 13/840,588, Non-Final Office Action dated Feb. 9, 2017, 25 pages.
BR1120140258783 received an office action dated Jan. 14, 2020, 7 pages.
Liu, F-Y, "Pulmonary Delivery Of Free Liposomal Insulin," Pharmaceutical Research, Kluwer Academic Publishers, New York, NY, vol. 10, No. 2, Feb. 1, 1993, 5 pages.
International Search Report and Written Opinion of PCT/US2011/020925 dated Mar. 14, 2011, 7 pages.
International Search Report and Written Opinion of PCT/US2011/020926 dated Mar. 14, 2011, 11 pages.
International Search Report and Written Opinion of PCT/US2013/034359 dated Jun. 28, 2013, 35 pages.
International Search Report (PCT/US/057971) dated Dec. 13, 2013; 3 pages.
European Search Report of EP 11733287 dated Jul. 12, 2013, 12 pages.
European Search Report for European Patent Application 11733286.6, dated Aug. 4, 2015, 5 pages.
EP Application No. 11733286.6 filed Jan. 12, 2011 received an Office Action dated Mar. 20, 2018, 4 pages.
Australian Examination Report of related Australian application No. 2011205443 dated Mar. 13, 2015, 4 pages.
Office Action of related Chinese Application No. 201180005839.9 dated Jun. 17, 2014, 16 pages.
Office Action of related Chinese application No. 201180005839.9 dated Mar. 3, 2015, 13 pages.
Office Action of related Mexican application No. MX/a/2012/008010 dated Jul. 15, 2014, 5 pages.
Office Action of related Mexican Patent Application No. MX/a/2012/008010 dated Nov. 12, 2014, 6 pages.
Office Action of related Mexican Application No. MX/a/2012/008010 dated Feb. 12, 2015, 2 pages.
Office Action of related Russian Application No. 2012134422 dated Oct. 20, 2014, 5 pages.
U.S. Appl. No. 15/165,662 received a Final Office Action dated Jan. 30, 2017, 16 pages.
U.S. Appl. No. 15/165,662 received a Final Office Action dated May 7, 2018, 18 pages.
U.S. Appl. No. 15/165,662 received a Non-Final Office Action dated Aug. 8, 2016, 16 pages.
U.S. Appl. No. 15/165,662 received a Non-Final Office Action dated Aug. 30, 2017, 16 pages.

(56) References Cited

OTHER PUBLICATIONS

U.S. Appl. No. 15/165,662 received a Non-Final Office Action dated Sep. 6, 2018, 18 pages.
U.S. Appl. No. 15/165,662 received an Advisory Action dated Jul. 10, 2017, 3 pages.
U.S. Appl. No. 15/165,662 received an Advisory Action dated Jul. 24, 2018, 3 pages.
U.S. Appl. No. 14/606,623 received a Notice of Allowance dated Dec. 14, 2016 4 pages.
U.S. Appl. No. 14/606,623 received a Notice of Allowance dated Apr. 18, 2016, 8 pages.
U.S. Appl. No. 14/606,623 received a Non-Final Office Action dated Mar. 8, 2016, 7 pages.
U.S. Appl. No. 14/039,254 received a Non-Final Office Action dated Feb. 10, 2014, 16 pages.
U.S. Appl. No. 14/039,254 received a Final Office Action dated Jun. 11, 2014, 18 pages.
U.S. Appl. No. 14/039,254 received a Notice of Allowance dated Mar. 18, 2015, 2 pages.
U.S. Appl. No. 14/039,254 received Notice of Allowance dated Dec. 24, 2014, 14 pages.
U.S. Appl. No. 14/039,254 received an Advisory Action dated Sep. 10, 2014, 3 pages.
U.S. Appl. No. 13/004,662 received a Notice of Allowance dated Nov. 24, 2014, 13 pages.
U.S. Appl. No. 13/004,662 received a Non-Final Office Action dated Apr. 18, 2014, 14 pages.
U.S. Appl. No. 13/004,662 received a Non-Final Office Action dated Oct. 10, 2013, 14 pages.
U.S. Appl. No. 13/004,662 received a Non-Final Office Action dated Jan. 22, 2013, 9 pages.
U.S. Appl. No. 13/004,662 received a Final Office Action dated Aug. 22, 2014, 16 pages.
U.S. Appl. No. 13/004,662 received a Final Office Action dated Jul. 18, 2013, 16 pages.
U.S. Appl. No. 13/004,662 received an Advisory Action dated Sep. 6, 2013, 3 pages.
U.S. Appl. No. 13/830,551 received a Non-Final Office Action dated Feb. 9, 2018, 23 pages.
U.S. Appl. No. 13/830,551 received a Non-Final Office Action dated May 26, 2017, 18 pages.
U.S. Appl. No. 13/830,551 received a Non-Final Office Action dated Apr. 11, 2016, 14 pages.
U.S. Appl. No. 13/830,551 received a Non-Final Office Action dated Feb. 27, 2015, 12 pages.
U.S. Appl. No. 13/830,551 received a Final Office Action dated Sep. 10, 2018, 18 pages.
U.S. Appl. No. 13/830,551 received a Final Office Action dated Oct. 3, 2017, 20 pages.
U.S. Appl. No. 13/830,551 received a Final Office Action dated Sep. 22, 2016, 16 pages.
U.S. Appl. No. 13/830,551 received a Final Office Action dated Jul. 31, 2015, 14 pages.
U.S. Appl. No. 13/830,511 received an Final Office Action dated Oct. 30, 2015, 45 pages.
U.S. Appl. No. 13/830,511 received an Final Office Action dated Jul. 26, 2016, 26 pages.
U.S. Appl. No. 13/830,511 received an Final Office Action dated Jan. 8, 2018, 38 pages.
U.S. Appl. No. 13/830,511 received an Non-Final Office Action dated Apr. 5, 2017, 29 pages.
U.S. Appl. No. 13/830,511 received an Non-Final Office Action dated Jun. 4, 2015, 36 pages.
U.S. Appl. No. 13/830,511 received an Non-Final Office Action dated Mar. 11, 2016, 45 pages.
U.S. Appl. No. 13/830,511 received an Non-Final Office Action dated May 15, 2018, 26 pages.
U.S. Appl. No. 13/830,511 received an Non-Final Office Action dated Mar. 16, 2015, 27 pages.
European Application No. EP13778248.8 received an Extended European Search report dated Oct. 26, 2015, 12 pages.
European Application No. EP13778248.8 received a Notice of Decision to Grant dated May 4, 2018, 1 page.
BR1120120171771 received an Office Action dated Feb. 27, 2020 3 pages. No English translation available.
BR1120120171771 received a Notice of Allowance dated Jul. 30, 2020, 1 page, no English translation available.
Brazilian Application No. BR1120140258783 received an Office Action, dated Oct. 13, 2021, 5 pages.
U.S. Appl. No. 17/874,531, Non-Final Office Action, dated Mar. 2, 2023, 21 pages.

\* cited by examiner

METHODS AND SYSTEMS FOR SUPPLYING AEROSOLIZATION DEVICES WITH LIQUID MEDICAMENTS

CROSS REFERENCE TO RELATED APPLICATIONS

This application is a continuation of U.S. Nonprovisional application Ser. No. 13/830,511, filed Mar. 14, 2013, which is a nonprovisional application claiming the benefit of U.S. Provisional Application No. 61/624,531, filed Apr. 16, 2012, the complete disclosures of which are herein incorporated by reference.

This application is a continuation-in-part of U.S. Nonprovisional application Ser. No. 15/165,662, filed May 26, 2016, which is a continuation of U.S. patent application Ser. No. 14/606,623, filed on Jan. 27, 2015, now U.S. Pat. No. 9,545,488, which is a continuation of U.S. patent application Ser. No. 14/039,254, filed on Sep. 27, 2013, now U.S. Pat. No. 9,004,061, which is a continuation of U.S. patent application Ser. No. 13/004,662, filed on Jan. 11, 2011, now U.S. Pat. No. 8,950,394, which claims priority from U.S. Provisional Application No. 61/335,769, filed on Jan. 12, 2010, the complete disclosures of which are herein incorporated by reference.

BACKGROUND OF THE INVENTION

Various types of inhalers exist for aerosolizing liquids. For example, U.S. Pat. No. 5,586,550, incorporated herein by reference, describes an inhaler that comprises a dispensing apparatus in which a membrane with tapered apertures is vibrated such that liquid in contact with a rear face of the membrane is dispensed from a front face of the membrane as an aerosol. Other examples of single dose inhaler systems and medicaments that may be aerosolized are described in U.S. Patent Publication Nos. 2011/0168172 and 2011/0168170, the disclosures of which are herein incorporated by reference.

One aspect of such inhalers is the need to supply a metered amount of liquid medicament to the dispensing apparatus so that the metered amount may be aerosolized and delivered to the patient's lungs. However, delivering a known quantity of a liquid medicament (that typically must be stored in a sterile environment) has proven to be challenging, particularly when the metered quantity needs to be dispensed in a controlled and repeatable fashion. Hence, this invention relates to ways for delivering such medicaments to inhalers for subsequent aerosolizing.

BRIEF SUMMARY OF THE INVENTION

One embodiment provides a method for supplying a metered amount of a liquid medicament to an aerosolizing device in a repeatable manner. The method utilizes an aerosolization device comprising a housing having a mouthpiece, a vibratable member within the housing and disposed to eject liquid droplets through the mouthpiece, a reservoir to hold the liquid medicament until aerosolized by the vibratable member, and an opening in the housing and in communication with the chamber. While described in connection with one specific type of inhaler, it will be appreciated that other types of aerosolization devices could be used with the methods described herein.

To supply a metered amount of liquid medicament, a dispenser is used that comprises an elongate dispenser body having a proximal end and a tip at a distal end through which a liquid medicament is dispensed. The dispenser further comprises a dispensing mechanism that operates to dispense a metered quantity of the liquid medicament from the tip each time the dispenser body is compressed.

One critical factor of the method is the manner in which the dispenser is held and operated by a user. To facilitate dispensing, the dispenser may be grasped with one hand such that the fingers wrap around the dispenser body, with the thumb closest to the proximal end and the last or pinky finger closest to the tip. The tip of the dispenser is inserted into the opening in the housing. Then, while grasping the dispenser in the manner described, the elongate body is forced toward the tip to cause the dispenser body to compress, thereby operating the dispensing mechanism and causing a metered quantity of the liquid medicament to eject into the chamber each time the dispenser body is compressed.

Because the prescription may call for more medicament than can be supplied with a single ejection from the dispenser, the process may be repeated for as many times as is needed to supply the prescribed amount into the chamber. This may be done with a "pumping action" where the user "pumps" the dispenser (causing it to compress with each pump), until the correct number of pumps have been supplied. For example, if the prescription calls for a certain volume of the liquid medicament, the dispenser may be pumped five times, with each pump dispensing a droplet having a metered volume of one-fifth the total volume.

In some cases, the tip may include at least one alignment feature that assists to keep the dispenser generally perpendicular to the housing while dispensing the liquid medicament. Once the metered amount has been dispensed into the chamber, the vibratable member is actuated to eject the dispensed liquid medicament as an atomized spray.

In another embodiment, the invention provides an exemplary aerosolization system. The system includes an aerosolization device comprising a housing having a mouthpiece, a vibratable member within the housing and disposed to eject liquid droplets through the mouthpiece, a reservoir to hold the liquid medicament until aerosolized by the vibratable member, and an opening in the housing that is in fluid communication with the chamber.

The system further includes a dispenser comprising an elongate dispenser body having a proximal end and a tip at a distal end through which a liquid medicament is dispensed. The dispenser further comprises a dispensing mechanism that operates to dispense a metered quantity of the liquid medicament from the tip each time the dispenser body is compressed. The dispenser is separate from the housing so that it may be manually interfaced with the aerosolization device.

Further, the opening defines an interface that engages with the tip such that when the tip is inserted into the opening, the interface stabilizes the dispenser in an upright orientation outside of the housing to permit the dispenser to be grasped with one hand to dispense the medicament. For example, this orientation permits a user to wrap the fingers around the dispenser body, with the thumb closest to the proximal end and the last finger closest to the tip, and while grasping the dispenser, forcing the elongate body toward the tip to cause the dispenser body to compress, thereby operating the dispensing mechanism and causing a metered quantity of the liquid medicament to eject into the chamber each time the dispenser body is compressed.

In one important aspect, the tip may include at least one alignment feature that assists to keep the dispenser generally perpendicular to the top surface of the housing while dispensing the liquid medicament. This alignment feature may comprise a circular step around the tip, a plurality of tabs protruding from the tip, and the like.

In yet another embodiment, the invention provides an exemplary method for supplying a metered amount of a liquid medicament to an aerosolizing device. The method utilizes an aerosolization device comprising a housing having a mouthpiece, a vibratable member within the housing and disposed to eject liquid droplets through the mouthpiece, and a reservoir to hold the liquid medicament until aerosolized by the vibratable member. The housing also includes a top surface and an opening in the top surface of the housing. The opening is in fluid communication with the chamber.

The method also utilizes a dispenser that comprises an elongate dispenser body having a proximal end and a tip at a distal end through which a liquid medicament is dispensed. The dispenser further comprises a dispensing mechanism that operates to dispense a metered quantity of the liquid medicament from the tip each time the dispenser body is compressed.

With this configuration, the tip is inserted into the opening in the housing such that the dispenser body is generally perpendicular to the top surface of the housing and is seated within the opening such that the dispenser body is self-standing outside of the housing. In this orientation, the dispenser body may be compressed to operate the dispensing mechanism and cause a metered quantity of the liquid medicament to eject into the chamber each time the dispenser body is compressed.

The dispenser may be repeatedly compressed to dispense multiple metered quantities of the liquid medicament into the chamber. Further, the tip may include one or more alignment features that assist to keep the dispenser generally perpendicular to the housing while dispensing the liquid medicament so that it may be aerosolized.

DETAILED DESCRIPTION OF THE INVENTION

Figure 1:
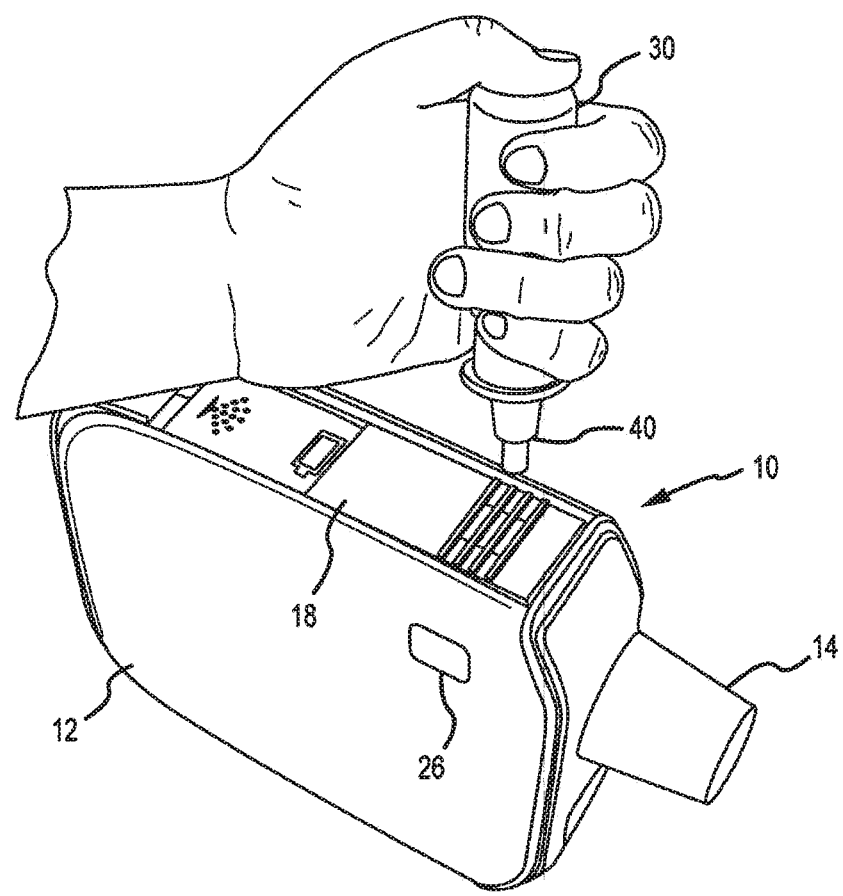
FIG. 1 illustrates one method for grasping a dispenser in preparation for delivering a metered amount of liquid medicament to an aerosolizing apparatus.

Certain aspects of the invention relate to techniques for dispensing metered quantities of a liquid medicament into an aerosolizing apparatus, also referred to as an inhaler. Although useful with a wide variety of aerosolizing devices, in some cases the liquid will be dispensed into an aerosolizing apparatus comprising a housing defining a dispensing outlet or mouthpiece, a vibratable membrane or mesh having a front face exposed at the outlet and a rear face for receiving a liquid to be dispensed, and a vibrating mechanism connected to the housing and operable to vibrate the membrane to dispense aerosol of the liquid through the membrane.

A variety of containers or dispensers may be used to store the liquid medicament, then to deliver a metered quantity of the liquid into a reservoir where it will contact the rear face of the membrane. In this way, a metered quantity of liquid is dispensable at the outlet or mouthpiece by operating the vibrating mechanism for an operating period sufficient to completely aerosolize the metered quantity at the rear face. The containers or dispensers will typically have a sealed region where the liquid is stored and a mechanism for dispensing a metered amount of liquid each time the mechanism is operated. For example, the container may be compressed or pumped to eject a droplet of a known volume.

Exemplary aerosol generators that may be used in such inhalers are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, and in U.S. Patent Publication Nos. 2011/0168172 and 2011/0168170, all incorporated herein by reference. These references describe exemplary aerosol generators and ways to manufacture such aerosol generators. Each are incorporated by reference for at least these features. The aerosol generators may comprise vibratable membranes having tapered aperture with a size in the range from about 3 µm to about 8 µm, preferably from about 3 µm to about 6 µm, and in some cases around 4 µm. The membrane may be domed shaped and be vibrated by an annular piezoelectric element that circumscribes the apertures. The diameter of the membrane may be in the range from about 5 mm to about 8 mm. The membrane may also have a thickness in the range from about 50 microns to about 70 microns. Typically, the membrane will be vibrated at a frequency in the range from about 50 kHz to about 150 kHz.

A variety of liquid medicaments may be dispensed from the container. For example, the liquid medicament may comprise an insulin formulation, such as a preservative free insulation, including any of those described in U.S. Patent Publication No. 2011/0168170, previously incorporated by reference. For example, a preservative free insulin formulation that may be dispensed may be free of any preservatives, including phenol, metacresol, chloro-cresol, thymol and mixtures thereof or the like. The absence of such preservatives enable the formulations to be aerosolized as a liquid spray using a vibrating mesh or aperture plate that operates at high frequencies. The absence of such preservatives permits a dosage of the formulation to come into contact with the vibrating mesh without substantial foaming of the formulation. In turn, the formulation may be aerosolized more quickly. Further, substantially all of the liquid is able to be aerosolized. Such formulations contain water in major and human insulin in minor amount. The formulations may also include various concentrations of human insulin. For example, the concentrations may be in the range from about 100 IU insulin/ml of formulation to about 1200 IU insulin/ml of formulation, and more preferably from about 200 IU insulin/ml of formulation to about 800 IU insulin/ml of formulation. In addition to water and human insulin, the formulations may also include zinc, acetate, chloride and sodium. The zinc ion and acetate ion come from the drug substance, e.g., the insulin. The chloride ion and sodium ion are added during dissolution of the insulin and adjustment of the pH. Merely by way of example, the NaCl concentration may be about 20 mM for an 800 IU insulin/ml formulation, about 10 mM for a 400 IU insulin/ml formulation, and about 5 mM for a 200 IU insulin/ml formulation.

Other liquid medicaments may also be dispensed. For example, such medicaments could include other protein formulations, asthma and COPD treatments, vaccines and pain relief treatments.

Referring now to the Figures, one exemplary method for dispensing a metered amount of medicament into an inhaler will be described. Shown in FIG. 1 is an inhaler 10 that is constructed of a housing 12 having a mouthpiece 14. Disposed within the housing is an aerosol generator comprising a vibratable mesh similar to those described herein, as well as electronics to control operation of the aerosol generator. The mesh is positioned to eject an aerosol through mouthpiece 14 when the mesh is vibrated. Housing 12 includes a top surface 13 with a slidable cover 18 is positioned over an opening 20 (see FIG. 2). Cover 18 is slid back is to expose opening 20. Further, opening 20 leads to a reservoir 22 or funnel (see FIGS. 3 and 4) that tapers toward a vibratable mesh 24 that is part of an aerosol generator that may be similar to any of those described herein. More specifically, mesh 24 has a rear face that is exposed to reservoir 22 so that when liquid is supplied to reservoir 22 it comes into contact with the rear face of mesh 24. When mesh 24 is vibrated (by actuating an "on" button 26 that energizes the aerosol generator) the liquid is ejected from the front face of mesh 24 as an atomized spray and is available for inhalation through mouthpiece 14.

Figure 5:
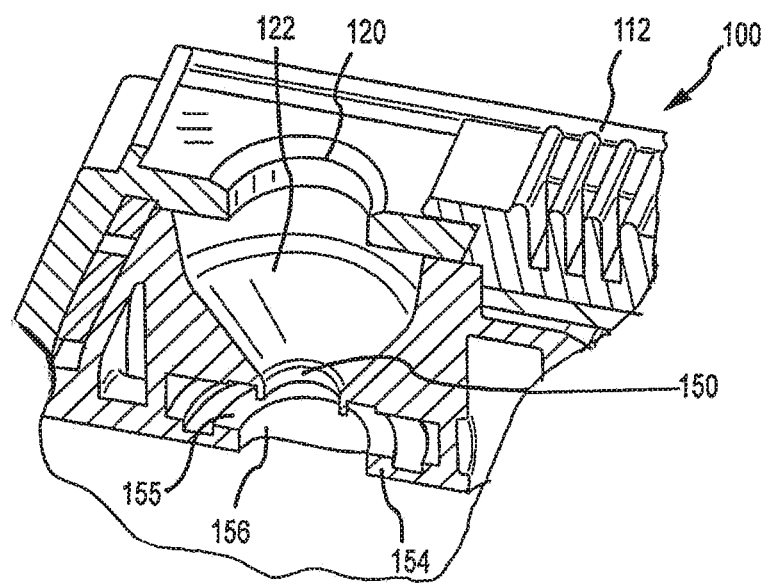
FIG. 5 is a cross sectional side view of another embodiment of an aerosolizing apparatus according to the invention.

FIG. 5 illustrates the internal components of an inhaler 100 that is similar to inhaler 10 as previously described. Inhaler 100 is constructed of a housing 112 that includes an opening 120 leads to a reservoir 122 that has an open bottom end 150 that funnels the dispensed liquid onto the rear face of a vibratable mesh (not shown) that is part of an aerosol generator 154 that has a vibratable element 155 (such as an annular piezoelectric transducer) that vibrates the mesh. Aerosol generator 154 has a circular opening 156 across which the mesh is disposed. When vibrated, the mesh ejects the liquid as an aerosolized spray into a capture chamber and to a mouthpiece. In this way, the aerosolized spray may be inhaled by inhaling from the mouthpiece.

Figure 3:
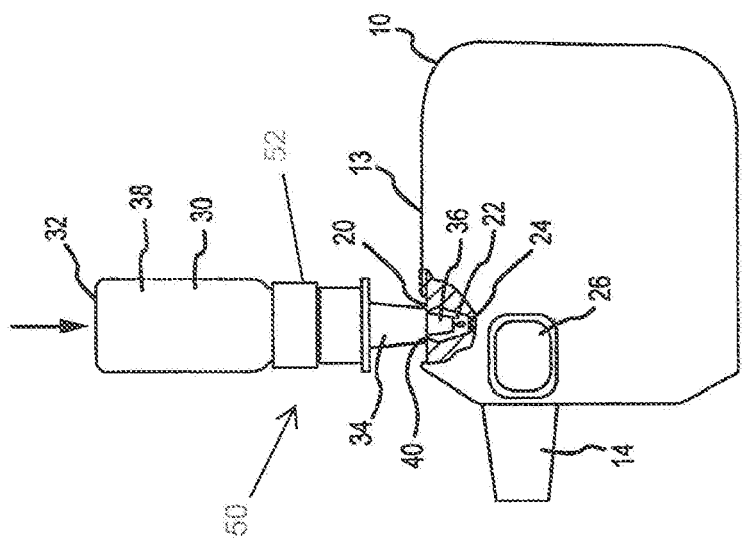
FIG. 3 illustrates the dispenser of FIG. 1 when initially inserted into the aerosolizing apparatus of FIG. 1.
Figure 4:
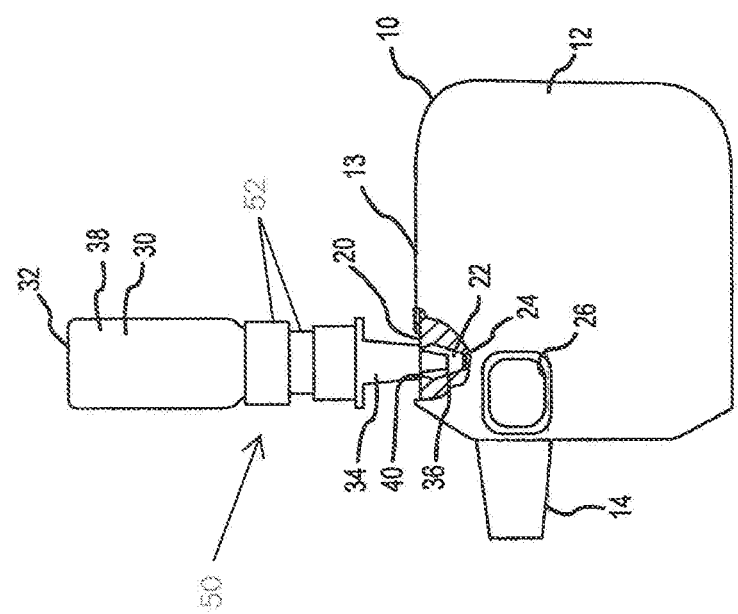
FIG. 4 illustrates the dispenser of FIG. 3 when compressed or pumped to deliver the liquid medicament.

In one embodiment, the liquid to be aerosolized is stored in a dispenser 30 that is best illustrated in FIGS. 3 and 4. Dispenser 30 may be conveniently described in terms of a proximal end 32 and a distal end 34 that terminates in a tip 36. Dispenser 30 further includes a canister 38 that stores the liquid medicament in a sterile environment. Dispenser 30 includes an internal valve such that distal end 34 may be moved relative to proximal end 32, thus compressing dispenser 30. In so doing, each time dispenser 30 is compressed (or "pumped") a metered volume of liquid is ejected into reservoir 22. For example, FIG. 3 shows dispensing mechanism 50 with a dispensing mechanism housing 52 in an uncompressed state. In FIG. 4, a force is applied to axially compress the dispensing mechanism 50 and the dispensing mechanism housing 52 to eject the droplet into the reservoir 22. A similar process may be used in connection with inhaler 100 where the liquid is injected into reservoir 122. This process may be repeated as many times as needed in order to dispense the proper volume of the liquid medicament into reservoir 22. After dispersing the desired amount of liquid medicament, dispenser 30 may be removed and stored for future use. Exemplary unit volumes that may be dispensed with each pump may be in the range from about 5 to about 100 microliters.

Tip 36 includes a shoulder 40 in the shape of an annular or circular step that serves as a stop to prevent further insertion of tip 34 into opening 20. Shoulder 40 is inset by a distance that is sufficient so that it not only serves as a stop by also permits tip 36 to seat within opening 20 in a stable position that is generally vertical to the top surface 13 of housing 12. As such, once dispenser 30 is placed into opening 20, it will be self-standing in a generally vertical orientation. This position permits a user to easily grasp the disperser 30 when ready to dispense a unit volume of the liquid to the aerosol generator. Although shown with a shoulder, other seating mechanisms could be used, such as a taper that matches with the taper of opening 20, protruding tabs or wings, detents, and the like.

Figure 2:
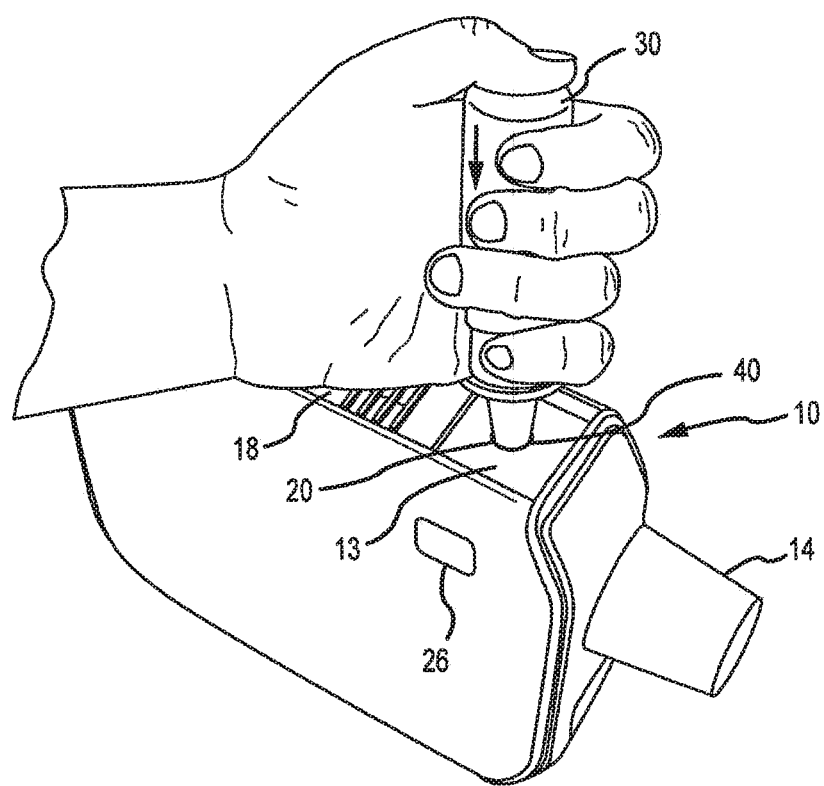
FIG. 2 illustrates the dispenser of FIG. 1 when inserted into the aerosolizing apparatus and compressed in order to deliver the liquid medicament.

One exemplary technique for operating dispenser 30 is illustrated in FIGS. 1 and 2. It will be appreciated that a similar process may be used in connection with inhaler 100. In FIGS. 1 and 2, dispenser 30 is grasped with one hand, such that the four fingers wrap around dispenser 30, mostly about canister 38. By using four fingers to grasp dispenser 30, a firm grip is achieved so that dispenser 30 may easily be pumped to eject the liquid. Further, the person's thumb may rest on proximal end 32 to apply a further compressive force. With the proper grip, cover 18 may be slid back and tip 34 placed into opening 20. As previously described, tip 34 includes a shoulder 40 that is wider than opening 20 so as to prevent tip 34 from coming into contact with mesh 24. Further, shoulder 40 may be designed so that tip 34 is sufficiently spaced-apart from mesh 24 so that when the full metered amount of the liquid is dispensed into reservoir 22, tip 34 does not come into contact with the dispensed liquid. In this way, when dispenser 30 is removed from the inhaler, it will not also remove some of the dispensed liquid. Typically, tip 34 will be spaced apart from mesh 24 by a distance that is in the range from about 5 mm to about 20 mm. Tip 34 may also be tapered, such as to match the taper of reservoir 22. The taper of reservoir 22 facilitates delivery of all the dispensed liquid onto the rear face of mesh 24, and the tapering of tip 34 prevents it from coming into contact with the walls of reservoir 22.

As best shown in FIG. 2, with tip 34 in place, the user presses canister 38 toward tip 34. At the same time, inhaler 10 is held in place. This causes dispenser 30 to compress. In turn, the internal valve is opened to permit a metered amount of liquid to be dispensed from tip 34 and into reservoir 22. Each time canister 38 is pressed downward, or pumped, another metered amount of liquid is ejected. This maneuver is performed as many times as is needed in order to supplied the prescribed dosage into reservoir 22.

By holding the dispenser 30 in the manner shown, this pumping action may easily occur. This is in contrast to a nasal spray dispenser, that is typically actuated in an upright manner by carefully and simultaneously compressing the proximal end with the middle and index finger (with the tip extending between the fingers) to the distal end of the dispenser container, that is held under equal pressure by the thumb. With this type of nasal sprayer, the spray occurs when sufficient pressure is applied equally to both ends. In contrast, dispenser 30 can be easily actuated by applying pressure solely to the distal end of the dispenser when the tip is engaged with the inhaler device. The inhaler device and mating features are constructed so that a metered amount of medicament is consistently delivered from the dispenser into the device and the user may do so with unregulated pressure, provided the force is greater than or equal to that required to compress the dispenser throughout its full range. If the inhaler device is loaded while placed on a table or any other freely supported surface, the force required to compress the dispenser into the device to the point of actuation is reduced by 50% when compared to the amount of force required to disperse a volume of liquid when holding both the device and dispenser (without the aid of a support surface).

Figure 6:
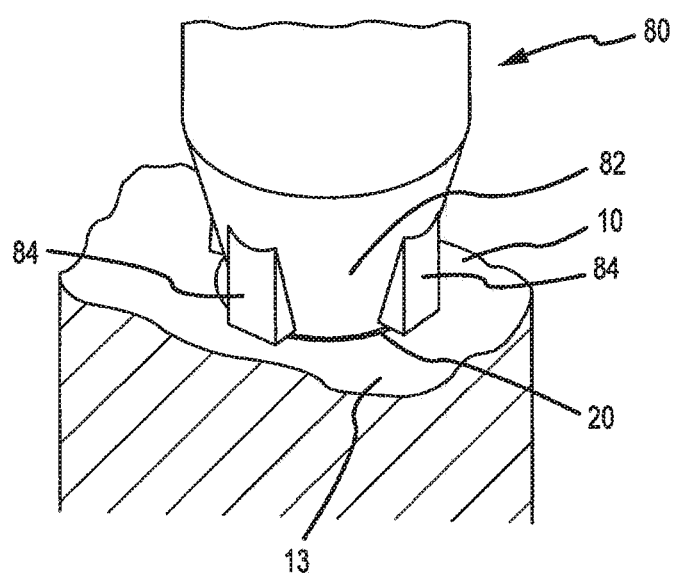
FIG. 6 illustrates another embodiment of a dispenser having ribs to facilitate positioning of the dispenser.

FIG. 6 illustrates an alternative embodiment of a dispenser 80 that may be used with inhaler 10 or inhaler 100. Dispenser 80 has a tip 82 at its distal end with multiple alignment features 84 that assist to properly align and position tip 82 within opening 20 in top surface 13. Alignment features 84 may have a variety of shapes, sizes and configurations. Although shown with four equally spaced apart features 84, it will be appreciated that other numbers may be used, such as only a single alignment feature. Features 84 serve as stops to limit insertion of tip 82 into opening 20. Features 84 also provide a tactile feel to let the user know when tip 82 has been properly inserted. When all four features 84 engage the surface of inhaler 10, dispenser 80 has been properly inserted and is ready to have a metered amount dispensed into inhaler 10. Further, features 84 serve to hold dispenser 80 in a generally vertical or perpendicular orientation relative to top surface 13. In this way, dispenser 80 is self-standing when inserted into opening 20 to make it easier for a user to grasp and dispense as described in connection with FIGS. 1 and 2.

The invention has now been described in detail for purposes of clarity and understanding. However, it will be appreciated that certain changes and modifications may be practiced within the scope of the appended claims.

What is claimed is:

1. A method for supplying a metered amount of a liquid medicament to an aerosolizing device, the method comprising:
providing an aerosolization device comprising a housing having an upward-facing surface, a bottom surface opposite the upward-facing surface, a lateral surface extending between the upward facing surface and the bottom surface, a mouthpiece disposed on the lateral surface, a vibratable member within the housing and disposed to eject liquid droplets through the mouthpiece, a reservoir to hold the liquid medicament until aerosolized by the vibratable member, and an opening defined in the upward-facing surface of the housing, the opening being in fluid communication with a chamber that funnels fluid to a surface of the vibratable member, wherein the bottom surface of the housing is substantially flat;
providing a dispenser comprising an elongate dispenser body having a proximal end and a tip at a distal end, wherein the dispenser further comprises a dispensing mechanism that operates to dispense a metered quantity of the liquid medicament from the tip each time the dispenser body is compressed;
inserting the tip into the opening in the housing, wherein the dispensing mechanism comprises a seating mechanism that maintains a distal end of the tip at a distance of between about 5 mm to about 20 mm from the vibratable member; and
compressing the dispenser body, thereby operating the dispensing mechanism and causing a metered quantity of the liquid medicament to eject into the chamber each time the dispenser body is compressed, wherein sidewalls defining a bottom end of the chamber are tapered from a bottom opening of the chamber to a position that is above the distal end of the tip when the tip is fully inserted within the opening.

2. A method as in claim 1, wherein compressing the dispenser body comprises forcing the elongate body toward the tip multiple times to dispense multiple metered quantities of the liquid medicament into the chamber, and wherein each compression dispenses a single metered quantity.

3. A method as in claim 1, wherein the seating mechanism includes at least one alignment feature, and wherein the alignment feature assists to keep the dispenser generally perpendicular to the housing while dispensing the liquid medicament.

4. A method as in claim 1, further comprising actuating the vibratable member to eject the dispensed liquid medicament as an atomized spray.

5. A method as in claim 1, further comprising sliding a cover away from the opening in the housing.

6. A method as in claim 1, wherein the opening defines an interface that is configured to stabilize the dispenser such that the dispenser is seated within the opening such that the dispenser body is self-standing in a vertical orientation relative to a top surface of the housing.

7. A method as in claim 1, wherein:
the tip is tapered;
an inner wall of the reservoir is tapered; and
a degree of taper of the tip matches a degree of taper of the inner wall.

8. A method as in claim 1, wherein:
the sidewalls defining the bottom end of the chamber comprise a continuous taper from the bottom opening to the position.

9. An aerosolization system, comprising:
an aerosolization device comprising a housing having an upward-facing surface, a bottom surface opposite the upward-facing surface, a lateral surface extending between the upward facing surface and the bottom surface, a mouthpiece disposed on the lateral surface, a vibratable member within the housing and disposed to be in fluid communication with the mouthpiece, a fluid reservoir that is positioned above and in fluid communication with the vibratable member, and an opening defined in the upward-facing surface of the housing, the opening being in fluid communication with a chamber that funnels fluid to a surface of the vibratable member, wherein the bottom surface of the housing is substantially flat; and
a dispenser comprising an elongate dispenser body having a proximal end and a tip at a distal end, wherein the dispenser further comprises a dispensing mechanism that is configured to dispense a metered quantity of liquid medicament from the tip each time the dispenser body is compressed, wherein the dispenser is separate from the housing;
wherein the opening defines an interface that engages with the tip such that when the tip is inserted into the opening, the interface stabilizes the dispenser in an upright orientation outside of the housing;
wherein the dispensing mechanism comprises a seating mechanism that maintains a distal end of the tip at a distance of between about 5 mm to about 20 mm from the vibratable member; and
wherein sidewalls defining a bottom end of the chamber are tapered from a bottom opening of the chamber to a position that is above the distal end of the tip when the tip is fully inserted within the opening.

10. A system as in claim 9, wherein the seating mechanism includes at least one alignment feature, and wherein the alignment feature assists to keep the dispenser generally perpendicular to a top surface of the housing while dispensing the liquid medicament.

11. A system as in claim 10, wherein the alignment feature comprises a circular step around the tip.

12. A system as in claim 11, wherein the alignment feature comprises a plurality of tabs protruding from the tip.

13. A system as in claim 9, further comprising a cover that is slidingly engaged with the housing and that covers the opening when in a closed position.

14. A system as in claim 9, wherein the interface is configured to stabilize the dispenser such that the dispenser is seated within the opening such that the dispenser body is self-standing in a vertical orientation relative to a top surface of the housing.

15. A system as in claim 9, wherein:
the tip is tapered;

an inner wall of the fluid reservoir is tapered; and a degree of taper of the tip matches a degree of taper of the inner wall.

16. A method for supplying a metered amount of a liquid medicament to an aerosolizing device, the method comprising:

providing an aerosolization device comprising a housing having an upward-facing surface, a bottom surface opposite the upward-facing surface, a lateral surface extending between the upward facing surface and the bottom surface, a mouthpiece disposed on the lateral surface, a vibratable member within the housing and disposed to eject liquid droplets through the mouthpiece, a reservoir to hold the liquid medicament until aerosolized by the vibratable member, and an opening defined in the upward-facing surface of the housing, wherein the bottom surface of the housing is substantially flat and wherein the opening is in fluid communication with a chamber that funnels fluid to a surface of the vibratable member;

providing a dispenser comprising an elongate dispenser body having a proximal end and a tip at a distal end, wherein the dispenser further comprises a dispensing mechanism that operates to dispense a metered quantity of the liquid medicament from the tip each time the dispenser body is compressed;

inserting the tip into the opening in the housing such that the dispenser body is generally perpendicular to the upward-facing surface of the housing and is seated within the opening such that the dispenser body is self-standing outside of the housing, wherein the dispensing mechanism comprises a seating mechanism that maintains a distal end of the tip at a distance of between about 5 mm to about 20 mm from the vibratable member; and compressing the dispenser body to operate the dispensing mechanism and cause a metered quantity of the liquid medicament to eject into the chamber each time the dispenser body is compressed, wherein sidewalls defining a bottom end of the chamber are tapered from a bottom opening of the chamber to a position that is above the distal end of the tip when the tip is fully inserted within the opening.

17. A method as in claim 16, further comprising repeatedly forcing the elongate body toward the tip to dispense multiple metered quantities of the liquid medicament into the chamber.

18. A method as in claim 16, wherein the seating mechanism includes at least one alignment feature, and wherein the alignment feature assists to keep the dispenser generally perpendicular to the housing while dispensing the liquid medicament.

19. A method as in claim 16, further comprising actuating the vibratable member to eject the dispensed liquid medicament as an atomized spray.

20. A method for supplying a metered amount of a liquid medicament to an aerosolizing device, the method comprising:

providing an aerosolization device comprising a housing having an upward-facing surface, a bottom surface opposite the upward-facing surface, a lateral surface extending between the upward facing surface and the bottom surface, a mouthpiece disposed on the lateral surface, a vibratable member within the housing and disposed to eject liquid droplets through the mouthpiece, a reservoir to hold the liquid medicament until aerosolized by the vibratable member, and an opening defined in the upward-facing surface of the housing, the opening being in fluid communication with a chamber that funnels fluid to a surface of the vibratable member, wherein the bottom surface of the housing is substantially flat;

providing a dispenser comprising an elongate dispenser body having a proximal end and a tip at a distal end through which the liquid medicament is dispensed, wherein the dispenser further comprises a dispensing mechanism that operates to dispense a same metered quantity of the liquid medicament from the tip each time the dispenser body is compressed;

inserting the tip into the opening in the housing, wherein the dispensing mechanism comprises a seating mechanism that maintains a distal end of the tip at a distance of between about 5 mm to about 20 mm from the vibratable member; and compressing the dispenser body, thereby operating the dispensing mechanism and causing the same metered quantity of the liquid medicament to eject into the chamber each time the dispenser body is compressed, wherein sidewalls defining a bottom end of the chamber are tapered from a bottom opening of the chamber to a position that is above the distal end of the tip when the tip is fully inserted within the opening.

* * * * *